United States Patent [19]

Kato et al.

[11] Patent Number: 4,931,474
[45] Date of Patent: Jun. 5, 1990

[54] ETHER DERIVATIVE AND AN ACARICIDAL OR INSECTICIDAL COMPOSITION COMPRISING SAID DERIVATIVE

[75] Inventors: Shoichi Kato, Ageo; Tatsumi Hayaoka, Tokyo, both of Japan

[73] Assignee: Nippon Kayaku Kabushiki Kaisha, Tokyo, Japan

[21] Appl. No.: 78,151

[22] Filed: Jul. 27, 1987

[30] Foreign Application Priority Data

Aug. 6, 1986 [JP]  Japan .................................. 61-184677

[51] Int. Cl.$^5$ ..................... A01N 59/02; C07C 147/14
[52] U.S. Cl. ..................................... 514/708; 514/651;
514/709; 514/712; 564/353; 564/354; 568/29;
568/30; 568/33; 568/36; 568/37; 568/44;
568/49; 568/52
[58] Field of Search ............... 564/353, 354; 568/44,
568/49, 37, 33, 52, 50, 36, 29, 30; 514/709, 712,
651, 708

[56] References Cited

U.S. PATENT DOCUMENTS

| | | | |
|---|---|---|---|
| 3,154,581 | 10/1964 | Dice | 564/354 |
| 3,542,874 | 11/1970 | Keizer et al. | 564/349 |
| 3,647,888 | 3/1972 | Rohr et al. | 568/585 |
| 3,723,524 | 3/1973 | Augstein | 564/165 |
| 3,766,238 | 10/1973 | Rohr et al. | 558/424 |
| 3,798,276 | 3/1974 | Bayer et al. | 568/586 |
| 3,813,444 | 5/1974 | Abe et al. | 568/30 |
| 3,821,312 | 6/1974 | Abe et al. | 568/44 |
| 3,857,954 | 12/1974 | Aoki et al. | 514/708 |
| 3,928,408 | 12/1975 | Hamman et al. | 558/302 |
| 3,957,865 | 5/1976 | Rohe et al. | 564/74 |
| 3,998,972 | 12/1976 | Farooq et al. | 514/712 |
| 4,147,805 | 4/1979 | Morrow | 514/651 |
| 4,243,681 | 1/1981 | Morrow et al. | 514/652 |
| 4,588,433 | 5/1986 | Schmitt et al. | 568/33 |

FOREIGN PATENT DOCUMENTS

| | | |
|---|---|---|
| 0007294 | 1/1980 | European Pat. Off. |
| 0015505 | 9/1980 | European Pat. Off. |
| 0043736 | 1/1982 | European Pat. Off. |
| 44536 | 1/1982 | European Pat. Off. |
| 2418572 | 11/1974 | Fed. Rep. of Germany |
| 2434660 | 2/1975 | Fed. Rep. of Germany |
| 2520145 | 11/1975 | Fed. Rep. of Germany |
| 2531312 | 5/1976 | Fed. Rep. of Germany |
| 2616755 | 10/1976 | Fed. Rep. of Germany |
| 2628478 | 1/1978 | Fed. Rep. of Germany |
| 2930608 | 2/1980 | Fed. Rep. of Germany |
| 2930728 | 2/1980 | Fed. Rep. of Germany |
| 56-36163 | 8/1981 | Japan |
| 1308191 | 2/1973 | United Kingdom |
| 2083022 | 3/1982 | United Kingdom |

OTHER PUBLICATIONS

T. Suzuki et al., Chem. Abst. vol. 105, No. 52253r (1986).
J. Chi, Chem. Abst. vol. 54, No. 4451h (1959).

*Primary Examiner*—Mary E. Ceperley
*Attorney, Agent, or Firm*—John P. White

[57] ABSTRACT

An ether derivative compound of the formula:

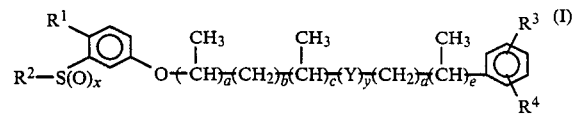

wherein $R^1$ is hydrogen, chloro, methyl or $(C_1-C_3)$-alkoxy, $R^2$ is $(C_1-C_6)$-alkyl, $R^3$ is hydrogen, chloro, bromo, fluoro, $-CF_3$, nitro, $(C_1-C_4)$-alkyl, methoxy, phenoxy or $(C_1-C_3)$-alkylthio, $R^4$ is hydrogen, chloro or methyl, Y is oxygen, sulfur, sulfinyl, sulfonyl, or imino, x is 0, 1 or 2, y is 0 or 1, a is 0 or 1, b is an integer of 0 to 6, c is 0 or 1, d is 0, 1 or 2, e is 0 or 1, except that all of a, b and c are zero.

3 Claims, No Drawings

ETHER DERIVATIVE AND AN ACARICIDAL OR INSECTICIDAL COMPOSITION COMPRISING SAID DERIVATIVE

DETAILED DESCRIPTION OF THE INVENTION

The present invention relates to a novel ether compound, which can be used as an acaricide, insecticide in paddy fields, uplands, orchards or forests, or for the purpose of exterminating hygienic insect pests.

Certain ether derivatives are known to be useful as an active ingredient of an acaricide.

Thus, 3-alkylthio(sulfinyl or sulfonyl)phenylether derivatives exhibiting an acaricidal activity are known, for example, as following compounds:

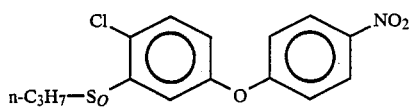

(Japanese Patent Publication No. 9732/1977)

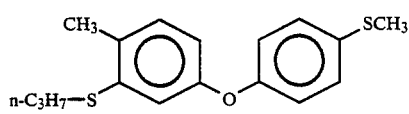

(Japanese Patent Publication No. 31932/1977)

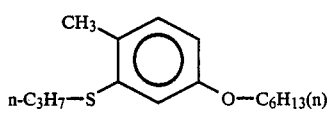

(Japanese Patent Publication No. 35162/1982)

The inventors of the present invention have performed intensive research to find a compound exhibiting acaricidal activity superior to the known compounds above-mentioned, on both spider mites which acquired a resistance to acaricides such as organophosphorus compounds and Dicofol (Kelthane®) widely used and highly susceptible spider mites, and furthermore, also exhibiting an insecticidal activity.

As a result of the research carried out according to the above-mentioned intention, the inventors of the present invention have found that 3-alkyl-thio (-sulfinyl, or -sulfonyl)phenyl phenylalkyl ether derivatives of the formula (I) below exhibit an excellent acaricidal activity of both spider mites which acquire a resistance to the known acaricides above-mentioned and highly susceptible spider mites, and further found also an insecticidal activity that was unknown about the known compound above-mentioned.

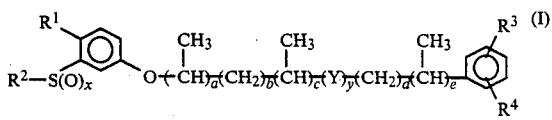

wherein $R^1$ is hydrogen, chlorine, methyl or $C_1$-$C_3$-alkoxy, $R^2$ is $C_1$-$C_6$ alkyl, $R^3$ is hydrogen, chlorine, bromine, fluorine, trifluoromethyl, nitro, $C_1$-$C_4$-alkyl, methoxy, phenoxy or $C_1$-$C_3$ alkylthio, $R^4$ is hydrogen, chlorine or methyl, Y is oxygen, sulfur, sulfinyl, sulfonyl or imino, x is 0, 1 or 2, y is 0 or 1, a is 0 or 1, b is an integer of 0 to 6, c is 0 or 1, d is an integer of 0 to 2 and e is 0 or 1, except that all of a, b and c are zero (0).

An ether derivative represented by the formula (I) can be prepared by the following processes.

(Process A)

The compound of the formula (I) can be obtained by reacting a compound represented by the formula:

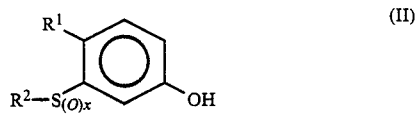

wherein $R^1$, $R^2$ and x are as defined above, or its alkali-metal salt with a compound represented by the formula:

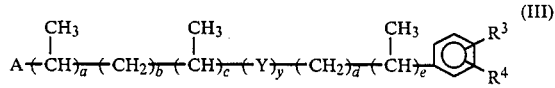

wherein $R^3$, $R^4$, Y, a, b, c, d, e and y are as defined above, and A represents halogen, mesyloxy or tosyloxy, except that all of a, b and c are zero without any solvent or in an inert organic solvent, if necessary, in the presence of an acid binding agent, at a temperature of $-10°$ to $130°$ C., preferably from room temperature to $100°$ C., for 0.5 to 24 hours. The molar proportion of a compound represented by the formula (II) to a compound represented by the formula (III) is usually 1:0.5 to 10, preferably 1:0.8 to 2.0. As a preferable inert organic solvent, aromatic hydrocarbons such as benzene, toluene and xylene, aliphatic hydrocarbons such as hexane, heptane and petroleum benzine, chlorinated hydrocarbons such as chloroform, dichloromethane and trichloroethylene, aprotic polar solvents such as dimethylformamide, dimethylacetamide and dimethylsulfoxide, ethers such as diisopropyl ether, diethyl ether, 1,2-dimethoxyethane, tetrahydrofuran, and dioxane, nitriles such as acetonitrile and propionitrile, and ketones such as acetone, diisopropyl ketone, methylethyl ketone can be used. As a preferable example of acid binding agents, alkali metal hydroxides such as NaOH and KOH, alkaline earth metal hydroxides such as Ca(OH)$_2$ Mg(OH)$_2$, alkali metal hydrides, alkyllithium reagents, alkali metal alcoholates such as sodium alcoholate, alkali metal oxides such as Na$_2$O and K$_2$O, alkali metal carbonates such as soda ash, alkali metal amides such as sodium amide, and aliphatic and aromatic tertiary amines such as triethyl amine, dialkylaniline and pyridine are mentioned. Silver oxide can be used as an acid binding agent also. In the present reaction, a phase transfer catalyst represented by tetra-n-butylammonium bromide and benzyl triethyl ammonium chloride may be also used, and, in this case, water may be used as one of solvents.

Further, a compound of the present invention can be also prepared by the following process, when y is 1, Y represents oxygen, sulfur or imino group, and except that all of a, b and c are zero in the general formula (I).

(Process B)

A compound of the present invention can be obtained by reacting a compound represented by the formula:

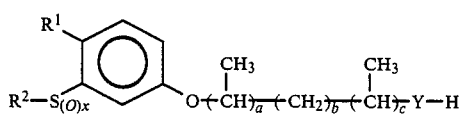 (IV)

wherein $R^1$, $R^2$, x, a, b and c are as defined above, and Y represents oxygen, sulfur or imino group, except that all of a, b and c are zero,
with a compound represented by the formula:

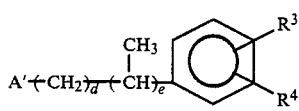 (V)

wherein $R^3$, $R^4$, d and e are as defined above, and A' represents halogen atom, mesyloxy or tosyloxy,
under much the same condition as described by the Process A.

Similarly, a compound of the general formula (I) wherein y=1 Y represents oxygen, sulfur or imino group except that all of a, b and c are zero, can be prepared also by the following process.

(Process C)

A compound of the present invention can be obtained by reacting a compound represented by the formula:

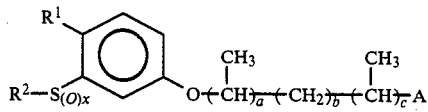 (VI)

wherein $R^1$, $R^2$, x, a, b, c and A are as defined above, except that all of a, b and c are zero,
with a compound represented by the formula

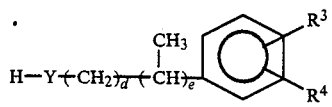 (VII)

wherein $R^3$, $R^4$, d and e are as defined above, and Y represents oxygen, sulfur or imino group,
under much the same condition as described by the Process A.

(Process D)

A compound of the formula (I) wherein x=1 or 2 and y=0, or y=1 and Y is oxygen, sulfonyl or imino group can be obtained also by preparing a compound of the formula:

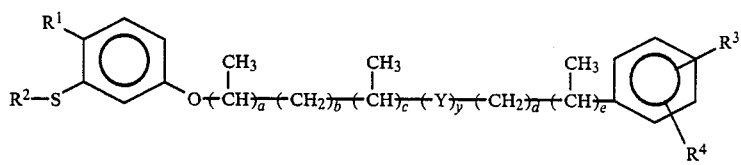 (VIII)

wherein $R^1$, $R^2$, $R^3$, $R^4$, a, b, c, d, e and y are as definded above, and Y represents oxygen, sulfonyl or imino group, except that $R^3$ is alkylthio group, and except that all of a, b and c are zero,
which corresponds to a compound of the formula (I) wherein x=0, by the above processes, and subsequently processing it with oxidizing agents such as hydrogen peroxide. Namely, a compound wherein x=1 can be obtained by reacting in acetic acid containing 1.0–3.0 molar proportion of hydrogen peroxide, preferably at 0° to 60° C. for 3 to 7 hours, or a compound wherein x=2 can be obtained by reaction in acetic acid containing 2.0 to 5.0 molar proportion of hydrogen peroxide, preferably at 15° to 90° C. for 2 to 24 hours in a favorable yield.

In these reactions, alcohols such as t-butanol, acetone, water as well as acetic acid, and also a mixture thereof can be used as a solvent.

An oxidizing agent which converts a compound of the formula (I) wherein x=0 to a compound corresponding to x=1, is, for example, sodium bromite, organic peroxide and halide, periodates, nitrogen oxides, ozone, metal oxide, singlet oxygen as well as hydrogen peroxide, and air oxidation and anodic oxidation may be applied.

An oxidizing agent which converts a compound of the formula (I) wherein x=0 or 1 to a compound corresponding to x=2, is, for example, peroxy acids, hydroperoxides, halognes, halogenating agents, ozone with a transition metal catalyst, potassium peroxysulfate, potassium permanganate, dinitrogen tetraoxide, sodium metaperiodate, osmium (VIII) and oxide, ruthenium (VIII) oxide, sodium dichromate, and nitric acid as well as hydrogen peroxide, and an electrode oxidation can be also applied.

A compound of the formula (I) wherein x=1, y=1 and Y is sulfinyl group can be obtained also by preparing a compound of the formula (I) wherein x=1, y=1 and Y is sulfur, represented by the formula:

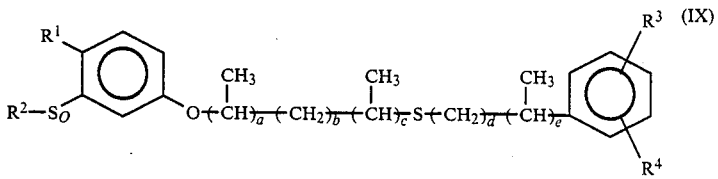 (IX)

wherein $R^1$, $R^2$, $R^3$, $R^4$, a, b, c, d and e are as defined above, except that all of a, b and c are zero, except that $R^3$ represents alkylthio group,
by the above-mentioned process, and subsequently by converting sulfur to sulfinyl group by the above oxidation process. In addition, a compound of the present invention can be obtained by preparing a compound of the formula (I) wherein x=0, y=1 and Y is sulfinyl group, represented by the formula:

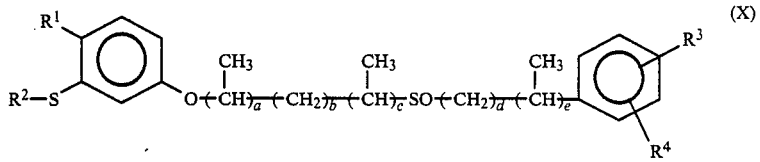

where $R^1$, $R^2$, $R^3$, $R^4$, a, b, c, d and e are as defined above, except that all of a, b and c are zero and except that $R^3$ represents alkylthio group,
by the above-mentioned process, and subsequently by converting sulfur to sulfinyl group by the above oxidation process.

Further, a compound of the formula (I) wherein x=2, y=1 and Y is sulfinyl or sulfonyl group, can be obtained by preparing a compound wherein x=2, y=1 and Y is sulfur, represented by the formula:

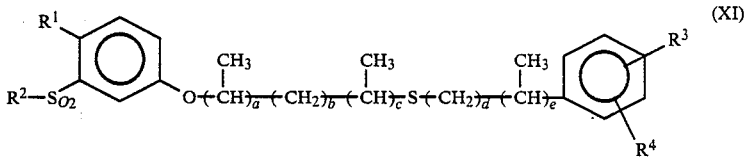

where $R^1$, $R^2$, $R^3$, $R^4$, a, b, c, d and e are as defined above, except that all of a, b and d c are zero and except that $R^3$ represents alkylthio group,
by the above-mentioned process, and subsequently by converting either sulfur to sulfinyl or sulfonyl, or sulfur at first to sulfinyl, oxidized subsequently to sulfonyl, by the above oxidation process.

In addition, the compound prepared by the Process D excludes a compound of the formula (I) wherein $R^3$ represents $(C_1-C_3)$alkylthio group.

Among the intermediate compounds used to prepare a compound of the present invention, a compound represented by the formula (II) wherein x=0 can be prepared by the process disclosed in Japanese Patent Publication No. 28787/1977, and a compound corresponding to x=1 and 2 can be prepared by applying an oxidizing process described above in Process D.

Furthermore, a compound represented by the general formula (III) can be prepared by the processes similar to known process, such as the processes (i) and (ii) as follows:

(i) A compound of the formula (III) wherein y=1 and Y represents oxygen, sulfur or imino group, can be prepared by the following process either 1 or 2 .

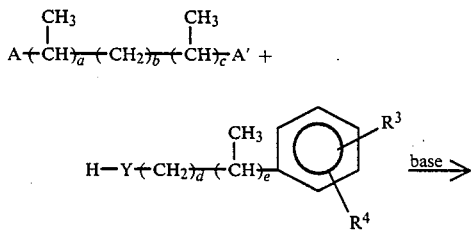

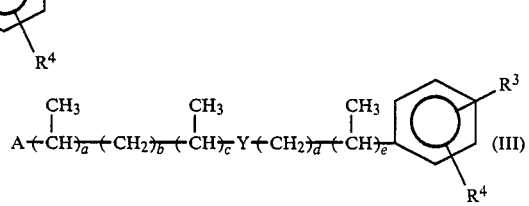

wherein $R^3$, $R^4$, a, b, c, d, and e are as defined above, Y represents oxygen, sulfur or imino group, and A and A', the same different with each other, represents halogen atom, mesyloxy or tosyloxy group with the exception that all of a, b, and c are zero:

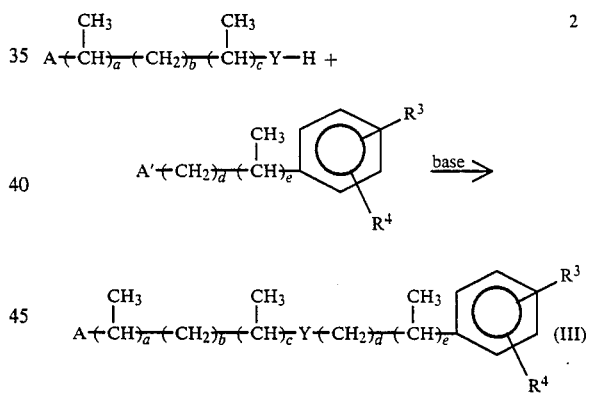

wherein $R^3$, $R^4$, a, b, c, d and e are as defined above, Y represents oxygen, sulfur or imino group, and A and A', the same or different with each other, represent halogen atom, mesyloxy or tosyloxy group, except that all of a, b, and c are zero.

(ii) A compound of the formula (III) wherein y=1 and Y represents sulfinyl or sulfonyl groups can be prepared by obtaining a compound wherein Y represents sulfur by the process (i), followed by oxidizing thereof as described in Process D.

A compound represented by the general formula (IV) can be prepared, for example, by the following process similar to known process:

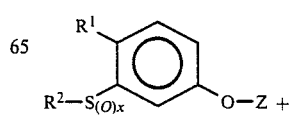

-continued $$A\text{-}(CH)_{\overline{a}}\text{-}(CH_2)_{\overline{b}}\overset{CH_3}{\underset{|}{\text{-}(CH)_{\overline{c}}}}A' \xrightarrow{\text{base}}$$

$$\underset{R^2-S(O)_x}{\overset{R^1}{\bigcirc}}\!\!\!\!\!\!\!\!\!\!\!\!\!\!\!\!\!\!\!\!\!\! O\text{-}(CH)_{\overline{a}}\overset{CH_3}{\underset{|}{\text{-}(CH_2)_{\overline{b}}}}\overset{CH_3}{\underset{|}{\text{-}(CH)_{\overline{c}}}}A' \xrightarrow{Y-H_2}$$

$$\underset{R^2-S(O)_x}{\overset{R^1}{\bigcirc}}\!\!\!\!\!\!\!\!\!\!\!\!\!\!\!\!\!\!\!\!\!\! O\text{-}(CH)_{\overline{a}}\overset{CH_3}{\underset{|}{\text{-}(CH_2)_{\overline{b}}}}\overset{CH_3}{\underset{|}{\text{-}(CH)_{\overline{c}}}}Y\text{-}H \quad (IV)$$

wherein R1, R2, x, a, b and c are as defined above, Y represents oxygen, sulfur or imino group, Z represents hydrogen or alkali metal except that all of a, b and c are zero, and A and A', the same different with each other, represents halogen atom, mesyloxy or tosyloxy group.

A compound of the formula (IV) can be prepared by the similar process of the preparation of the above compound (IV)

$$\underset{R^2-S(O)_x}{\overset{R^1}{\bigcirc}}\!\!\!\!\!\!\!\!\!\!\!\!\!\!\!\!\!\!\!\!\!\! O-Z \;+$$

$$A'\text{-}(CH)_{\overline{a}}\overset{CH_3}{\underset{|}{\text{-}(CH_2)_{\overline{b}}}}\overset{CH_3}{\underset{|}{\text{-}(CH)_{\overline{c}}}}A' \xrightarrow{\text{base}}$$

$$\underset{R^2-S(O)_x}{\overset{R^1}{\bigcirc}}\!\!\!\!\!\!\!\!\!\!\!\!\!\!\!\!\!\!\!\!\!\! O\text{-}(CH)_{\overline{a}}\overset{CH_3}{\underset{|}{\text{-}(CH_2)_{\overline{b}}}}\overset{CH_3}{\underset{|}{\text{-}(CH)_{\overline{c}}}}A \quad (VI)$$

wherein $R^1$, $R^2$, x, a, b and c are defined as above, Z is alkali metal or hydrogen, A and A' are same or diferent halogen, mesyloxy or tosyloxy except that all of a, b and c are zero.

As examples of $C_1$–$C_3$ alkoxy group in $R^1$ of a compound of the present invention represented by the formula (I), methoxy, ethoxy and n-propoxy may be mentioned; as examples of $C_1$–$C_6$-alkyl group in $R^2$, methyl, ethyl, n-propyl, isopropyl, n-butyl, s-butyl, isobutyl, t-butyl, n-pentyl, 2,2-dimethyl-n-propyl and n-hexyl may be mentioned; and as examples of $C_1$–$C_3$ alkylthio group in $R^3$, methylthio, ethylthio, n-propylthio may be mentioned.

In the present invention, the preferable compound of the formula (I) are those wherein $R^1$ is hydrogen, chloro or methyl,
$R^2$ is ($C_1$–$C_6$)-alkyl,
$R^3$ is hydrogen, chloro, bromo, fluoro, —$CF_3$, nitro, methyl, ethyl, t-butyl, methoxy, phenoxy, methylthio, ethylthio, n-propylthio,
$R^4$ is hydrogen, chloro or methyl,
Y is oxygen, sulfur, sulfinyl or sulfonyl,
x is 0, 1 or 2,
y is 0 or 1,
a is 0 or 1,
b is an integer of 0 to 6,
c is 0 or 1,
d is 0, 1 or 2,
e is 0 or 1,
except that all of a, b and c are zero.

The more preferable compound of the formula (I) are those wherein
$R^1$ is chloro or methyl,
$R^2$ is ethyl, n-propyl, n-butyl, isobutyl, n-amyl, n-hexyl,
$R^3$ is hydrogen, chloro, fluoro, —$CF_3$, nitro, methyl, ethyl, t-butyl, methoxy, phenoxy, methlthio, ethylthio, n-propylthio,
$R^4$ is hydrogen, chloro or methyl,
Y is oxygen, sulfur, sulfinyl or sulfonyl,
x is 0 or 1,
y is 1,
a is 0 or 1,
b is an integer of 1 to 6,
c is 0 or 1,
d is 0, 1 or 2,
e is 0 or 1 and
the sum of a, b, c, d and e is seven and below.

The most preferable compound of the formula (I) are those wherein $R^1$ is chloro or methyl,
$R^2$ is n-propyl,
$R^3$ is hydrogen, chloro, fluoro, —$CF_3$, methyl, t-butyl, methoxy, methylthio or n-propylthio,
$R^4$ is hydrogen,
Y is oxygen or sulfur,
x is 0,
y is 1,
a is 0 or 1,
b is an integer of 1 to 6,
c is 0 or 1,
d is 0 or 1,
e is 0 or 1 and
the sum of a, b, c, d and e is seven and below.

The compounds of the present invention may be used alone if desired, but they are generally formulated by blending suitable adjuvants to improve or stabilize the effects thereof and used as such or after diluted if necessary. The compounds of the invention can be formulated in the conventional manners well-known in the art without any special limitation in any convenient form such as dust, granule, micro granule, wettable powder, flowable, emulsion, microcapsule, oil, aerosol, heating fumigant (e.g. mosquito repellent of an incense type or electric type), fuming agent such a fogging, non-heating fumigant, or toxic feed.

Examples of said adjuvants are carrier (i.e. diluent) and other adjuvants such as a spreader, emulsifying agent, wetting agent, dispersing agent, fixing agent or disintegrator. Examples of the liquid carrier are aromatic hydrocarbons such as toluene or xylene; alcohols such as methanol, butanol or glycol; ketones such as acetone; amides such as di-methylformamide; sulfoxides such as dimethyl sulfoxide; methylnaphthalene; cyclohexane; animal or vegetable oils; fatty acids; fatty acid esters or the like as well as petroleum distillates such as kerosine or gas oil.

Examples of the solid carrier are clay, kaolin, talc, diatomaceous earth, silica, calcium carbonate, montmorillonite, bentonite, feldspar, quartz alumina or saw dust.

Surfactants are generally used as an emulsifying or dispersing agent. Examples of them are anionic, cationic, non-ionic and ampholytic surfactants such as sodium salt of higher alcohol sulfate, stearyltrimethylammonium chloride, polyoxyethylene alkylphenyl ether or laurylbetaine.

Examples of the spreaders are polyoxyethylene nonylphenyl ether and polyoxyethylene lauryl ether. Examples of the wetting agent are polyoxyethylene nonylphenyl ether and dilkyl suffosuccinate. Examples of the fixing agent are carboxymethylcellulose and polyvinyl alcohol. Examples of the disintegrator are sodium ligninsulfonate and sodium lauryl sulfate.

Furthermore, it is possible to blend two or more compounds of the present invention to obtain an improved insecticidal or acaricidal activity. In addition, it is also possible to use a compound of the present invention simultaneously with other physiologically active substances such as pyrethroids, e.g., allethrin, phthalthrin, permethrin, decamethrin, fenvalerate, or α-cyano-3-penoxybenzyl 2,2-dichloro-1-(4-ethoxyphenyl)-cyclopropane-1-carboxylate, and various isomers thereof, pyrethrum extract, organophosphorus pesticides, e.g., DDVP, fenitrothion, diazinon or temefos, carbamate pesticides, e.g., NAC, MTMC, BPMC or pirimor, other pesticides, acaricides, bactericides, nematicides, herbicides, plant growth regulators, fertilizers, BT, insect hormones or other pesticides, thereby affording a multi-purpose composition which exhibits an improved effect and further a synergistic effect, if things go well.

It is further possible to increase the effect of the composition several-fold by adding synergists for pyrethroids such as piperonyl butoxide, sulfoxide or safroxane.

Although the compounds of the present invention are stable to light, heat, oxidation or the like, antioxidant or ultraviolet absorber such as phenols, e.g., BHT or BHA, arylamines, e.g., α-naphthylamine or benzophenone compounds may be added as a stabilizer to prepare a composition which exhibits a higher stability, if desired.

The content of active ingredients in the composition of the present invention varies depending on the conditions of use such as formulation form or application method, and is usually from 0.2 to 95% by weight, preferably from 0.5 to 80% by weight, although the active ingredient may be used alone in a special case.

The composition of the present invention may be used in an amount which depends on the conditions such as formulation form, season or method for application. Generally, it is used in an amount of 10 to 300 g/10a (a=100 m$^2$), and preferably 15 to 200 g/10a (in terms of the active ingredient) for the control of insect pests in agriculture and horticulture, forestry or pasturage and in an amount of 2 to 200 mg/m$^2$, preferably 5 to 100 mg/m$^2$ (in terms of the active ingredient) for the purpose of exterminating hydienic insect pests. For example, from 15 to 120 g/10a of the active ingredient is used in the case of dust, 30 to 240 g/10a thereof is used in the case of granule and 40 to 250 g/10a thereof is used in the case of emulsion. However, it may be possible, or even necessary, to use the active ingredient in an amount which is outside the range as specified above, in a special case.

The insect pests on which the pesticides and acaricides of the present invention are effective are as follows; HEMIPTIERA such as *Nephotettix cincticeps, Sogatella furcifera, Nilaparavta lugens, Laodelphax striatellus, Riptortus clavatus, Nezara viridula, Stephanitis nashi, Trialeurodes vaporariorum, Aphis gossypii, Myzus persicae* and *Unaspis yanonensis*; LEPIDOPTERA such as *Phyllonorycter ringoneella, Plutella xylostella, Promalactis inonisema, Adoxophyes orana, Leguminivora glycinivorella, Cnaphalocrocis medinalis, Chilo suppressalis, Ostrinia furnacalis, Mamestra brassicae, Pseudaletia separata, Spodoptera litura, Parnara guttata* and *Pieris rapae crucivora*; COLEOPTERA such as *Anomala cuprea, Popillia japonica, Echinocnemus sogameus, Lissorhoptrus oryzophilus, Anthonomus grandis, Oulema oryzae, Diabrotica undecimpunctata, Leptinotarsa decemtineata, Anthrenus verbasci, Tenebroides manuritanicus, Sitophilus zeamais, Henosepilachna vigintioctopunctata, Callosobrunchus chinesis, Monochamus alternatus* and *Aulacophora femoralis*; HYMENOPTERA and as *Athalia rosae japonensis* and *Arge similis*; DIPTERA such as *Culex pipiens fatigans, Aedes aegypti, Asphondylia sp., Hylemya platura, Musca domestica vicina, Dacus cucurbitae* and *Agromyza oryzae*; APHANIPTERA such as *Pulex irritans, Xenopsylla cheopis* and *Ctenocephalides canis*; THYSANOPTERA such as *Scirtothrips dorsalis, Thrips tabaci, Thrips palmi* and *Baliothrips biformis*; ANOPLURA such as *Pediculus humanus corporis* and *Pthirus pubis*; PSCOPTERA such as *Trogium pulsatorium* and *Liposcelis bostrychophus*; ORTHOPTERA such as *Gryllotalpa africana, Locusta migratoria, Oxya yezoensis, Blattella germanica* and *Periplaneta fuliginosa* and ACRINA such as *Tetranychus urticae, Panonychus citri, Tetranychus cinnabarinus, Tetranychus kanzawai, Panonychus ulmi, Tetranychus viennensis, Aculus pelekassi, Polyphagotarsonemus latus, Oligonychus hondoensis, Epitrimerus pyri, Steneotarsonermus pallidus, Tenuipalpus zhizhilashviliae, Brevipalpus obovatus, Bryobia praetiosa, Calepitrimerus vitis, Tyrophagus putrescenticae* and *Rhrizoglyphus echinopus.*

The compound of the present invention is an excellent acaricide and insecticide, and exhibits lethal effects on adults, eggs and nymphae in every stage of spider mites, and can present also various insect pests effectively by contacting with the compound, even without phytotoxicity to the host crops.

Now, the present invention will be described by Examples.

SYNTHESIS EXAMPLE

Synthesis Example 1

Synthesis of 1-(4-chlorobenzyloxy)-4-methyl-3-n-propylthiobenzene (Compound No. 18) by Process A 12 g of 4-methyl-3-n-propylthiophenol, 10.7 g of 4-chlorobenzyl chloride and 6.4 g of anhydrous potassium carbonate were stirred in 50 ml of acetone. After stirring under reflux for 8 hours, the reaction mixture was cooled and poured in 200 ml of water, followed by 2 times of extraction with 100 ml, of toluene. The toluene layer was washed by water, and dried with anhydrous sodium sulfate. The residue obtained by distilling off the solvent was recrystallized to give 13.8 g of the intended 1-(4-chlorobenzyloxy)-4-methyl-3-n-propylthiobenzene (yield: 71.4%) as a colorless crystal. m.p. 35° to 36° C.

PMR(CDCl$_3$) δ:1.01(t,3H), 1.61(m,2H), 2.27(s,3H), 2.82(t,2H), 4.97(s,2H), 6.63(d-d,1H), 6.84(d,1H), 7.03(d,1H), 7.32(s,4H) ppm.

Synthesis Example 2

Synthesis of 1-benzylthio-3-(4-methyl-3-n-propylthiophenoxy)-n-propane (Compound No. 36) by Process A 1 Synthesis of the intermediate, 1-benzylthio-3-chloro-n-propane:

24.8 g of benzyl mercaptan, 37.6 g of 1-bromo-3-chloro-n-propane, 3 g of tetrabutylammonium bromide and 100 ml of 20% aqueous solution of sodium hydroxide were drastically stirred at room temperature for 5 hours, then at 50° C. for 3 hours.

The reaction mixture was poured into 200 ml of water, and extracted 2 times by each 150 ml of toluene. The toluene layer was washed by 5% aqueous solution of sodium hydroxide, water and saturated NaCl aq., then dried with anhydrous sodium sulfate. The residue obtained by distilling off the solvent was distilled to give 33.5 g of the intended 1-benzylthio-3-chloro-n-propane (yield: 83.4%) as a colorless oil. b.p. 120° to 121° C./1.5 mm Hg.

2 Synthesis of the intended 1-benzylthio-3-(4-methyl-3-n-propylthiophenoxyl-n-propane:

1.8 g of 4-methyl-3-n-propylthiophenol, 0.2 g of benzyltetraethylammonium chloride, 10 ml of 40% aqueous solution of sodium hydroxide, 1 ml of toluene, and 2.0 g of 1-benzylthio-3-chloro-n-propane, obtained by 1 , were drastically stirred at 80° C., and so after 7 hours the reaction was finished. After cooling, the reaction mixture was poured into 100 ml of water, and extracted 2 times with 150 ml of toluene. The toluene layer was washed with water, and the solvent was distilled off therefrom. The obtained residue was purified by silica-gel column chromatography (developing solvent: toluene+n-hexane) to give 3.0 g of the intended 1-benzylthio-3-(4-methyl-3-n-propylthiophenoxy)-n-propane (yield: 86.6%) as a colorless oil. $n_D^{25}$ 1.5904.

PMR(CDCl$_3$) δ:1.03(t,3H), 1.65(m,2H), 1.98(m,2H), 2.27(s,3H), 2.59(t,2H), 2.85(t,2H), 3.70(s,2H), 3.98(t,2H), 6.57(d-d,1H), 6.79(d,1H), 7.02(d,1H), 7.28(s,5H) ppm.

Synthesis Example 3

Synthesis of 1-(4-t-butylbenzylthio)-3-(4-methyl-3-n-propylthiophenoxy)-n-propane (Compound No. 88) by Process B:

1 Synthesis of the intermediate 1-chloro-3-(4-methyl-3-n-propylthiophenoxy)-n-propane:

36.4 g of 4-methyl-3-n-propylthio-phenol, 35 g of 3-bromo-1-chloro-n-propane and 3 g of tetrabutylammonium bromide were added into 10% aqueous solution of sodium hydroxide, and this mixture was stirred drastically for 2 hours at room temperature, then for 6 hours at 50° C. After the reaction was finished, the mixture was poured into 200 ml of water, and extracted 2 times by 200 ml of toluene. After the toluene layer was washed with water, toluene was distilled off, and the residue thus obtained was purified by silica-gel column chromatography (developing solvent: toluene+n-hexane) to give 40 g of the intended 1-chloro-3-(4-methyl-3-n-propylthiophenoxy)-n-propane (yield: 77.3%) as a colorless oil, $n_D^{25}$ 1.5505.

2 Synthesis of the intermediate 3-(4-methyl-3-n-propylthiophenoxy)-n-propyl mercaptan:

2.6 g of 1-chloro-3-(4-methyl-3-n-propyl-thiophenoxy)-n-propane, obtained by 1 , and 1.2 g of thiourea was stirred in 15 ml of 95% ethanol under reflux for 5 hours. The residue obtained by concentration was added to a solution of 10 g of potassium hydroxide and 50 ml of water, and heated to 70°–80° C. for 5 hours with stirring.

After cooling, the solution was acidified by adding concentrated hydrochloric acid dropwise thereto, then after addition of 50 ml of benzene, the obtained benzene layer was collected. The residue obtained by distilling off benzene was promptly purified by silica-gel column chromatography (developing solvent; ethyl acetate+n-hexane) to give 1.2 g of the intended 3-(4-methyl-3-n-propylthiohenoxy)-n-propyl mercaptan (yield: 46.8%) as a colorless oil.

PMR(CDCl$_3$) δ:1.00(t,3H), 1.37(s,1H), 1.65(m,2H), 1.99(t,2H), 2.23(s,3H), 2.68(m,m,4H), 3.86(t,2H), 6.36(d-d,1H), 6.56(d,1H), 6.80(d,1H), ppm.

3 Synthesis of 1(4-t-butylbenzylthio)-3-(4-methyl-3-n-propylthiophenoxy)-n-propane:

5 g of sodium hydroxide was dissolved in 10 ml of water. To this solution, 1.2 g of 3-(4-methyl-3-n-propylthiophenoxy)-n-propyl mercaptan obtained by 2 , 0.2 g of benzyltriethylammonium chloride, 1 ml of toluene and 1.0 g of 4-t-butylbenzyl chloride were added, and this mixture was stirred drastically at 80° to 90° C. for 5 hours. After cooling, 50 ml of toluene was added thereto, and the toluene layer was collected. The toluene layer was washed with water, then dried over anhydrous sodium sulfate. The residue obtained by distilling off toluene, was purfied by silica-gel column chromatography (developing solvent: toluene+n-hexane) to give 1.0 g of the intended 1-(4-t-butylbenzylthio)-3-(4-methyl-3-n-propylthiophenoxy)-n-propane (yield: 55.2%) as a colorless oil. $n_D^{25}$ 1.5706.

PMR(CDCl$_3$) δ:1.04(t,2H), 1.31(s,9H), 1.70(m,2H), 2.05(m,2H), 2.28(s,3H), 2.62(t,2H), 2.87(t,2H), 3.69(s,2H), 400(t,2H), 6.59(d-d,1H), 6.80(d,1H), 7.02(d,1H), 8.27(d,4H) ppm.

Synthesis Example 4

Synthesis of 1-(4-bromophenylthio)-5-(4-methyl-3-n-propylthiophenoxy)-n-pentane (Compound No. 89) by Process C 1 Sythesis of the intermediate, 1-bromo-5-(4-methyl-3-n-propylthiophenoxy)-n-pentane:

A mixture of 36.5 g of 4-methyl-3-n-propylthiophenol, 11.5 g of 1,5-dibromopentane, 80 ml of water, 0.5 g of tetrabutylammonium bromide and 10 ml of toluene was stirred drastically and heated at 80° to 90° C. At this temperature, a solution of 8.6 g of sodium hydroxide and 20 ml of water was added dropwise to the mixture during 1 hour. The reaction was finished by stirring for 2 hours after the dropwise addition. After cooling, the reaction mixture was added with 150 ml of toluene, and separated to layers. A toluene layer was washed with water, and dried over anhydrous sodium sulfate. Then, the residue obtained by distilling off toluene and an excess of 1,5-dibromopentane under reduced pressure, was purified by silica-gel column chromatography (developing solvents: toluene+n-hexane) to give 45.9 g of the intended 1-bromo-5-(4-methyl-3-n-propylthiophenoxy)-n-pentane (yield: 69.3%) as a colorless oil. $n_D^{25}$ 1.5569.

2 Synthesis of 1-(4-bromophenylthio)-5-(4-methyl-3-n-propylthiophenoxy)-n-pentane:

10 g of sodium hydroxide was dissolved in 20 ml of water, and then added with 2.0 g of 4-bromothiophenol, 0.5 g of tetrabutylammonium bromide, 3 ml of toluene and 3.3 g of 1-bromo-5(4-methyl-3-n-propylthiophenoxy)-n-pentane obtained by 1 , followed by drastic stirring at 80° to 90° C. for 4 hours. After cooling, the reaction solution was poured into 100 ml of water, and extracted two times by 150 ml of toluene. The toluene layer was washed with water and saturated solution of common salt, and distilled to remove the solvent. The obtained residue was purified by silica-gel column chromatography (developing solvents: toluene+n-hexane) to give 3.5 g (yield: 79.6%) of the intended 1-(4-bromophenylthio)-5-(4-methyl-3-n-propylthiophenoxy)-n- pentane as a colorless crystal. Furthermore, it was recrystallized by n-hexane to give m.p. 42° to 43° C.

PMR(CDCl$_3$) δ:1.03(t,3H), 1.65(m,8H), 2.28(s,3H), 2.86(m,4H), 3.91(t,2H), 6.57(d-d,1H), 6.80(d,1H), 7.03(d,1H), 7.15(d,2H), 7.37(d,2H), ppm.

Synthesis Example 5

Synthesis of 2-benzylthio-1-(4-methyl-3-n-propylthiophenoxy)-n-propane (Compound No. 72) by Process C 1 Synthesis of the intermediate 2-(4-methyl-3-n-propylthiophenoxy)-isopropanol:

10 g of 4-methyl-3-n-propylthiohenol, 0.5 g of tetrabutylammonium bromide, 10 ml of toluene and 20% aqueous solution of sodium hydroxide were stirred drastically, and added dropwise with 5 g of propylene oxide at room temperature. Subsequent stirring was continued at 70° C. for 5 hours to finish the reaction. After cooling, 100 ml of water and 100 ml of toluene were added to the reaction mixture, and the separated toluene layer was collected. The toluene layer was washed by 100 ml of water and dried over anhydrous sodium sulfate.The residue obtained by distilling off toluene was purified by silica-gel column chromatography (developing solvents: ethyl acetate+n-hexane) to give 5.8 g (yield: 53.0%) of the intended 2-(4-methyl-3-n-propylthiophenoxy)-isopropanol as a colorless oil. $n_D^{25}$ 1.5496.

2 Synthesis of the intermediate 1-(4-methyl-3-n-propylthiophenoxy)-2(4-tolylsulfonyloxy)-n-propane:

5.8 g of 2-(4- methyl-3-n-propylthiophenoxy)-isopropanol, obtained by 1 , was dissolved in 8 ml of pyridine, and cooled at −20° C. Under stirring, 5.1 g of 4-tolysulfonyl chloride was added little by little to the solution. After addition, it was warmed gradually to room temperature, and stirred at room temperature for 3 hours, followed by pouring in a mixture of 15 ml of 35% hydrochloric acid and 150 ml of ice water. The mixture was extracted two times by 150 ml of toluene, and the toluene layer was washed by water, and dried over anhydrous sodium sulfate. The solid residue obtained by distilling off the solvents, was recrystallized by the solvent mixture of toluene and n-hexane to give 6.3 g (yield: 66.3%) of the intended 1-(4-methyl-3-n-propylthiophenoxy)-2-(4-tolylsulfonyloxy)-n-propane as a pale yellow crystal. m.p. 53° to 54° C.

3 Synthesis of 2-benzylthio-1-(4-methyl-3-n-propylthiophenoxy)-n-propane:

2.0 g of benzylmercaptan, 0.5 g of tetrabutylammonium bromide and 5.2 g of 1-(4-methyl-3-n-propylthiophenoxy)-2-(4-tolylsulfonyloxy)-n-propane obtained by 2 , were added to 35 ml of 10% aqueous solution of sodium hydroxide, and stirred drastically at 55° to 60° C. for 6 hours. After cooling, 50 ml of water and 100 ml of toluene were added to the solution under stirring, and the separated toluene layer was collected. The toluene layer was washed by water, and dried over anhydrous magnesium sulfate. The residue obtained by distilling off the solvent, was purified by silica-gel column chromatography (developing solvent: toluene+n-hexane) to give 4.5 g (yield: 96.2%) of the object 2-benzylthio-1-(4-methyl-3-n-propylthiophenoxy)-n-propane as a colorless oil, $n_D^{25}$ 1.5875.

PMR(CDCl$_3$) δ:1.03(t,3H), 1.34(d,3H), 1.64(m,2H), 2.27(s,2H), 2.84(t,2H), 2.97(m.1H), 3.83(s,2H), 3.90(m,2H), 6.52(d-d,1H), 6.78(d,1H), 7.01(d,1H), 7.29(s,5H) ppm.

Synthesis Example 6

Synthesis of 1-(4-methyl-3-n-propylsulfinylphenoxy)-2-phenoxyethane (Compound No. 32) by Process D 1 Synthesis of 1-(4-methyl-3-n-propylthiophenoxy)-2-phenoxyethane (Compound No. 31) by Process A:

3.6 g of potassium hydroxide was dissolved in 50 ml of methanol, whereto 10 g of 4-methyl-3-n-propylthiophenol was added, and the mixture was concentrated and dried to give potassium salt of 4-methyl-3-n-propylthiophenol. It was dissolved by adding 50 ml of N,N-dimethylacetamide. The whole solution was cooled in an ice bath, and added dropwise with 8.6 g of 1-chloro-2-phenoxyethane under stirring. After addition, the temperature was gradually raised to room temperature, and subsequently heated to 50° C. while stirring for 4 hours. After cooling, the content was poured in 200 ml of water, and extracted 2 times with 150 ml of toluene. The toluene layer was washed with water, and dried over anhydrous sodium sulfate. The residue obtained by distilling off the solvent, was purified by silica-gel column chromatography (developing solvents: toluene+n-hexane) to give 15 g (yield: 90.3%) of the intended 1-(4-methyl-3-n-propylthiophenoxy)-2-phenoxyethane as a colorless crystal. It was recrystallized by cyclohexane to show m.p. 72.5° to 73° C.

2 Synthesis of 1-(4-methyl-3-n-propyl-sulfinylphenoxy)-2-phenoxyethane:

5.6 g of 1-(4-methyl-3-n-propylthiophenoxy)-2-phenoxyethane obtained by 1 , was dissolved in 30 ml of acetic acid and 5 ml of acteone and cooled down below 10° C. 3 ml of aqueous hydrogen peroxide was added thereto dropwise, then the temperature was raised again to room temperature. After it was stirred at room temperature for 2 hours, the contents were poured into 200 ml of an ice water. It was extracted 2 times with 100 ml of toluene, and the toluene layer was washed 2 times by 5% aqueous solution of sodium hydroxide, and 2 times by water, followed by drying over anhydrous magnesium sulfate. The residue obtained by distilling off the solvent, was recrystallized by the solvent mixture of toluene and n-hexane to give 5.6 g (yield: 95.1%) of the intended 1-(4-methyl-3-n-propyl-sulfinylphenoxy)-2-phenoxyethane as a colorless crystal. m.p. 115° to 116° C.

PMR(CDCl$_3$) δ:1.06(t,3H), 1.57 to 2.00(m,2H), 2.29(s,3H), 2.71(t,2H), 4.35(s,4H), 6.90 to 7.52 (m,8H) ppm.

Synthesis Example 7

Synthesis of 1-benzylsulfinyl-3-(4-methyl-3-n-propylsulfinulphenoxy)-n-propane (Compound No. 50) by Process A 1 Synthesis of the intermediate 4-methyl-3-n-propylsulfinylphenol:

5 g of 4-methyl-3-n-propylthiophenol was dissolved in 30 ml of acetic acid, and while cooled by ice, added dropwise with 4.7 g of 35% hydrogen peroxide. After that, it was gradually warmed to room temperature again, and then stirred for 2 hours. the reaction mixture was poured into 150 ml of iced water, and extracted two times with 50 ml of benzene. The benzene layer was washed 2 times with a saturated aqueous sodium bicarbonate, then by water. It was dried over anhydours sodium sulfate, followed by distilling off the solvent, to give 4.7 g (yield: 86.5%) of the intended 4-methyl-3-n-propylsulfinylphenol as a colorless crystal. It can be recrystallized by ethanol+petroleum ether, to show m.p. 84° to 85° C.

2  Synthesis of an intermediate 1-benzylsulfinyl-3-chloro-n-propane:

1.2 g of 1-benzylthio-3-chloro-n-propane, synthesized by 1 of Synthesis Example 2 was dissolved in 50 ml of acetic acid, and 8.7 g of 35% aqueous hydrogen peroxide was added thereto dropwise under stirring below 10° C. After that, it was warmed gradually to room temperature again, then stirred further for 4 hours. The reaction mixture was poured in 300 ml of iced water, and extracted 2 times by each 150 ml of methylene chloride. The methylene chloride layer was washed 2 times with 5% aqueous solution of sodium hydroxide, followed by water, and dried over anhydrous magnesium sulfate. A colorless solid residue was obtained by distilling off methylene chloride. It was washed by n-hexane to give 12.6 g (yield: 96.9%) of the object 1-benzylsulfinyl-3-chloro-n-propane as a colorless crystal. m.p. 70° to 71° C.

3  Synthesis of 1-bnezylsulfinyl-3-(4-methyl-3-n-propylsulfinyl-phenoxy)-n-propane:

0.9 g of potassium hydroxide was dissolved in 30 ml of methanol, wherein 2.7 g of 4-methyl-3-n-propylsulfinylphenol, obtained by 1 , was added, and the solution was concentrated. The obtained potassium salt of 4-methyl-3-n-propylsulfinylphenol was dried well and dissolved in 30 ml of N,N-dimethylacetamide. 2.8 g of 1-benzylsulfinyl-3-chloro-n-propane obtained by 2 , was added thereto under stirring. The reaction mixture was stirred at 70° C. for 3 hours, and poured into 300 ml of ice water. It was extracted 2 times by 100 ml of methylene chloride. The methylene chloride layer was washed 2 times with 5% aqueous solution of sodium hydroxide, followed by water, and dried over anhydrous sodium sulfate. The solid residue obtained by distilling off methylene chloride was recrystallized by toluene+n-hexane to give 3.0 g (yield: 61.4%) of the intended 1-benzylsulfinyl-3-(4-methyl-3-n-propylsulfinylphenoxy)-n-propane. m.p. 92° to 94° C.

PMR(CDCl$_3$)  1.08(t,3H), 1.50 to 2.08(m,2H), 2.26(m,2H), 2.30(s,3H), 2.60 to 2.95(m,4H), 4.02(s,2H), 4.12(t,2H), 6.87(d-d,1H), 7.11(d,1H), 7.20 to 7.55(bs,6H) ppm.

Representative compounds of the present invention, which were prepared according to the process for preparation similar to the procedure described in above Synthesis Examples, are shown in Table 1.

TABLE 1

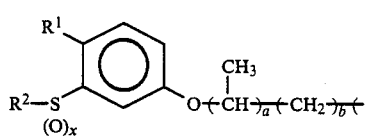 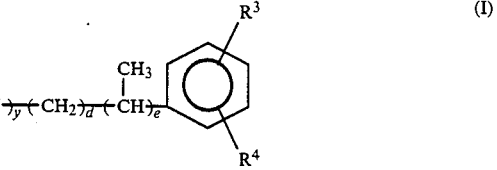

(I)

| Compound No. | R$^1$ | R$^2$ | x | a | b | c | y | Y | d | e | R$^3$ | R$^4$ | Physical property n$_D^{25}$(mp.), (bp.) |
|---|---|---|---|---|---|---|---|---|---|---|---|---|---|
| 1 | H | n-C$_3$H$_7$ | 0 | 0 | 1 | 0 | 0 | — | 0 | 0 | H | H | (bp. 196–199° C./4 mmHg) |
| 2 | H | n-C$_3$H$_7$ | 0 | 0 | 1 | 0 | 0 | — | 0 | 0 | 4-CH$_3$ | H | (bp. 154–157° C./0.5 mmHg) |
| 3 | H | n-C$_3$H$_7$ | 1 | 0 | 1 | 0 | 0 | — | 0 | 0 | 4-CH$_3$ | H | (mp. 53–55° C.) |
| 4 | H | n-C$_3$H$_7$ | 2 | 0 | 1 | 0 | 0 | — | 0 | 0 | 4-CH$_3$ | H | (mp. 106–107.5° C.) |
| 5 | H | n-C$_3$H$_7$ | 0 | 0 | 1 | 0 | 0 | — | 0 | 0 | 2-Cl | H | (bp. 183–185° C./1.0 mmHg) |
| 6 | H | n-C$_3$H$_7$ | 0 | 0 | 1 | 0 | 0 | — | 0 | 0 | 4-Cl | H | (bp. 180–184° C./1.5 mmHg) |
| 7 | H | n-C$_3$H$_7$ | 1 | 0 | 1 | 0 | 0 | — | 0 | 0 | 4-Cl | H | n$_D^{25}$ 1.5910 |
| 8 | H | n-C$_3$H$_7$ | 2 | 0 | 1 | 0 | 0 | — | 0 | 0 | 4-Cl | H | (mp. 103–105° C.) |
| 9 | H | n-C$_3$H$_7$ | 0 | 0 | 1 | 0 | 0 | — | 0 | 0 | 2-Cl | 4-Cl | (bp. 176–178° C./0.5 mmHg) |
| 10 | H | n-C$_3$H$_7$ | 1 | 0 | 1 | 0 | 0 | — | 0 | 0 | 2-Cl | 4-Cl | n$_D^{25}$ 1.5990 |
| 11 | H | n-C$_3$H$_7$ | 2 | 0 | 1 | 0 | 0 | — | 0 | 0 | 2-Cl | 4-Cl | (mp. 68–69.5° C.) |
| 12 | H | n-C$_3$H$_7$ | 0 | 0 | 1 | 0 | 0 | — | 0 | 0 | 3-Cl | 4-Cl | (bp. 180–183° C./0.5 mmHg) |
| 13 | H | n-C$_3$H$_7$ | 2 | 0 | 1 | 0 | 0 | — | 0 | 0 | 3-Cl | 4-Cl | (mp. 76.5–77.5° C.) |
| 14 | H | n-C$_3$H$_7$ | 0 | 0 | 1 | 0 | 0 | — | 0 | 0 | 4-NO$_2$ | H | n$_D^{25}$ 1.6074 |
| 15 | H | n-C$_3$H$_7$ | 1 | 0 | 1 | 0 | 0 | — | 0 | 0 | 4-NO$_2$ | H | n$_D^{25}$ 1.5990 |
| 16 | H | n-C$_3$H$_7$ | 2 | 0 | 1 | 0 | 0 | — | 0 | 0 | 4-NO$_2$ | H | (mp. 76.5–78.5° C.) |
| 17 | H | n-C$_3$H$_7$ | 0 | 0 | 1 | 0 | 1 | O | 0 | 0 | 3-SC$_3$H$_7$(n) | H | n$_D^{25}$ 1.5898 |
| 18 | CH$_3$ | n-C$_3$H$_7$ | 0 | 0 | 1 | 0 | 0 | — | 0 | 0 | 4-Cl | H | (mp. 35–36° C.) |
| 19 | CH$_3$ | n-C$_3$H$_7$ | 1 | 0 | 1 | 0 | 0 | — | 0 | 0 | 4-Cl | H | n$_D^{25}$ 1.5866 |
| 20 | CH$_3$ | n-C$_3$H$_7$ | 2 | 0 | 1 | 0 | 0 | — | 0 | 0 | 4-Cl | H | (mp. 76–78° C.) |
| 21 | CH$_3$ | n-C$_3$H$_7$ | 0 | 0 | 1 | 0 | 0 | — | 0 | 0 | 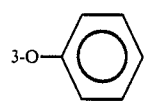 | H | n$_D^{25}$ 1.5998 |
| 22 | CH$_3$ | n-C$_3$H$_7$ | 1 | 0 | 1 | 0 | 0 | — | 0 | 0 | 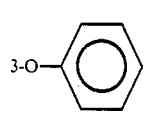 | H | n$_D^{25}$ 1.5944 |
| 23 | CH$_3$ | n-C$_3$H$_7$ | 2 | 0 | 1 | 0 | 0 | — | 0 | 0 | 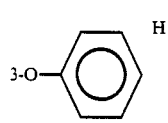 | H | n$_D^{25}$ 1.5912 |

TABLE 1-continued $$R^2-S(O)_x-\underset{R^1}{C_6H_3}-O+CH(CH_3)\rightarrow_a+CH_2\rightarrow_b+CH(CH_3)\rightarrow_c+Y\rightarrow_y+CH_2\rightarrow_d+CH(CH_3)\rightarrow_e-\underset{R^3,R^4}{C_6H_3}\quad (I)$$

| Compound No. | $R^1$ | $R^2$ | x | a | b | c | y | Y | d | e | $R^3$ | $R^4$ | Physical property $n_D^{25}$(mp.), (bp.) |
|---|---|---|---|---|---|---|---|---|---|---|---|---|---|
| 24 | $CH_3$ | $n$-$C_3H_7$ | 0 | 0 | 2 | 0 | 0 | — | 0 | 0 | H | H | $n_D^{25}$ 1.5798 |
| 25 | $CH_3$ | $n$-$C_3H_7$ | 0 | 1 | 0 | 0 | 0 | — | 0 | 0 | H | H | $n_D^{25}$ 1.5745 |
| 26 | $CH_3$ | $n$-$C_3H_7$ | 1 | 1 | 0 | 0 | 0 | — | 0 | 0 | H | H | $n_D^{25}$ 1.5736 |
| 27 | $CH_3$ | $n$-$C_3H_7$ | 0 | 0 | 3 | 0 | 0 | — | 0 | 0 | H | H | (bp. 193–195° C./1 mmHg) |
| 28 | $CH_3$ | $n$-$C_3H_7$ | 1 | 0 | 3 | 0 | 0 | — | 0 | 0 | H | H | $n_D^{25}$ 1.5706 |
| 29 | $CH_3$ | $n$-$C_3H_7$ | 2 | 0 | 3 | 0 | 0 | — | 0 | 0 | H | H | (mp. 59–61° C.) |
| 30 | $CH_3$ | $n$-$C_3H_7$ | 0 | 0 | 1 | 0 | 1 | S | 0 | 0 | H | H | $n_D^{25}$ 1.6164 |
| 31 | $CH_3$ | $n$-$C_3H_7$ | 0 | 0 | 2 | 0 | 1 | O | 0 | 0 | H | H | (mp. 72.5–73° C.) |
| 32 | $CH_3$ | $n$-$C_3H_7$ | 1 | 0 | 2 | 0 | 1 | O | 0 | 0 | H | H | (mp. 115–116° C.) |
| 33 | $CH_3$ | $n$-$C_3H_7$ | 0 | 0 | 1 | 0 | 1 | S | 0 | 0 | 4-Cl | H | $n_D^{25}$ 1.6170 |
| 34 | $CH_3$ | $n$-$C_3H_7$ | 0 | 0 | 2 | 0 | 1 | S | 0 | 0 | 4-Cl | H | $n_D^{25}$ 1.6070 |
| 35 | $CH_3$ | $n$-$C_3H_7$ | 0 | 0 | 2 | 0 | 1 | O | 0 | 0 | 3-$SC_3H_7$(n) | 4-$CH_3$ | (mp. 72–73° C.) |
| 36 | $CH_3$ | $n$-$C_3H_7$ | 0 | 0 | 3 | 0 | 1 | S | 1 | 0 | H | H | $n_D^{25}$ 1.5904 |
| 37 | $CH_3$ | $n$-$C_3H_7$ | 0 | 0 | 3 | 0 | 1 | S | 0 | 0 | 4-Cl | H | $n_D^{25}$ 1.6020 |
| 38 | $CH_3$ | $n$-$C_3H_7$ | 0 | 0 | 6 | 0 | 1 | S | 0 | 0 | 4-Cl | H | (mp. 42–43° C.) |
| 39 | $CH_3$ | $n$-$C_3H_7$ | 0 | 0 | 5 | 0 | 1 | S | 0 | 0 | 4-Cl | H | (mp. 47–48° C.) |
| 40 | $CH_3$ | $n$-$C_3H_7$ | 0 | 0 | 2 | 0 | 1 | O | 2 | 0 | 3-$SC_3H_7$(n) | 4-$CH_3$ | (mp. 75–76° C.) |
| 41 | $CH_3$ | $n$-$C_3H_7$ | 0 | 0 | 4 | 0 | 1 | S | 1 | 0 | H | H | $n_D^{25}$ 1.5802 |
| 42 | $CH_3$ | $n$-$C_3H_7$ | 0 | 0 | 4 | 0 | 1 | S | 1 | 0 | 4-Cl | H | $n_D^{25}$ 1.5898 |
| 43 | $CH_3$ | $n$-$C_3H_7$ | 0 | 0 | 3 | 0 | 1 | S | 1 | 0 | 4-Cl | H | $n_D^{25}$ 1.5640 |
| 44 | $CH_3$ | $n$-$C_3H_7$ | 0 | 0 | 3 | 0 | 1 | S | 1 | 0 | 4-$CH_3$ | H | $n_D^{25}$ 1.5831 |
| 45 | $CH_3$ | $n$-$C_3H_7$ | 0 | 0 | 5 | 0 | 1 | S | 1 | 0 | H | H | $n_D^{25}$ 1.5799 |
| 46 | $CH_3$ | $n$-$C_3H_7$ | 0 | 0 | 6 | 0 | 1 | S | 1 | 0 | H | H | $n_D^{25}$ 1.5732 |
| 47 | $CH_3$ | $n$-$C_3H_7$ | 1 | 0 | 3 | 0 | 1 | S | 1 | 0 | H | H | $n_D^{25}$ 1.5857 |
| 48 | $CH_3$ | $n$-$C_3H_7$ | 0 | 0 | 3 | 0 | 1 | SO | 1 | 0 | H | H | (mp. 86–87° C.) |
| 49 | $CH_3$ | $n$-$C_3H_7$ | 0 | 0 | 3 | 0 | 1 | $SO_2$ | 1 | 0 | H | H | (mp. 83–84° C.) |
| 50 | $CH_3$ | $n$-$C_3H_7$ | 1 | 0 | 3 | 0 | 1 | SO | 1 | 0 | H | H | (mp. 92–94° C.) |
| 51 | $CH_3$ | $n$-$C_3H_7$ | 1 | 0 | 3 | 0 | 1 | $SO_2$ | 1 | 0 | H | H | (mp. 99–99.5° C.) |
| 52 | Cl | $n$-$C_3H_7$ | 0 | 0 | 3 | 0 | 1 | S | 1 | 0 | H | H | $n_D^{25}$ 1.5979 |
| 53 | $CH_3$ | $n$-$C_3H_7$ | 0 | 0 | 2 | 0 | 1 | S | 1 | 0 | H | H | $n_D^{25}$ 1.5953 |
| 54 | $CH_3$ | $n$-$C_3H_7$ | 1 | 0 | 2 | 0 | 1 | S | 1 | 0 | H | H | $n_D^{25}$ 1.5909 |
| 55 | $CH_3$ | $n$-$C_3H_7$ | 0 | 0 | 3 | 0 | 1 | S | 1 | 0 | 4-$OCH_3$ | H | $n_D^{25}$ 1.5899 |
| 56 | $CH_3$ | $n$-$C_3H_7$ | 0 | 0 | 3 | 0 | 1 | O | 1 | 0 | H | H | $n_D^{25}$ 1.5612 |
| 57 | $CH_3$ | $n$-$C_3H_7$ | 1 | 0 | 3 | 0 | 1 | O | 1 | 0 | H | H | $n_D^{25}$ 1.5580 |
| 58 | $CH_3$ | $n$-$C_3H_7$ | 0 | 0 | 1 | 0 | 1 | S | 1 | 0 | H | H | $n_D^{25}$ 1.5993 |
| 59 | $OCH_3$ | $n$-$C_3H_7$ | 0 | 0 | 3 | 0 | 1 | S | 1 | 0 | H | H | $n_D^{25}$ 1.5931 |
| 60 | $OC_3H_7$(n) | $n$-$C_3H_7$ | 0 | 0 | 3 | 0 | 1 | S | 1 | 0 | H | H | $n_D^{25}$ 1.5758 |
| 61 | $CH_3$ | $n$-$C_3H_7$ | 0 | 0 | 4 | 0 | 1 | S | 1 | 0 | 4-$CH_3$ | H | $n_D^{25}$ 1.5801 |
| 62 | $OCH_3$ | $C_2H_5$ | 0 | 0 | 3 | 0 | 1 | S | 1 | 0 | H | H | $n_D^{25}$ 1.5971 |
| 63 | $CH_3$ | $n$-$C_3H_7$ | 0 | 0 | 3 | 0 | 1 | NH | 1 | 0 | H | H | $n_D^{25}$ 1.5718 |
| 64 | $CH_3$ | $n$-$C_3H_7$ | 0 | 0 | 2 | 0 | 1 | S | 2 | 0 | H | H | $n_D^{25}$ 1.5776 |
| 65 | $CH_3$ | $n$-$C_3H_7$ | 0 | 0 | 3 | 0 | 1 | S | 0 | 0 | H | H | $n_D^{25}$ 1.5969 |
| 66 | $CH_3$ | $n$-$C_3H_7$ | 0 | 0 | 4 | 0 | 1 | S | 0 | 0 | H | H | (mp. 35.5–36° C.) |
| 67 | Cl | $n$-$C_3H_7$ | 1 | 0 | 3 | 0 | 1 | S | 1 | 0 | H | H | $n_D^{25}$ 1.5869 |
| 68 | Cl | $n$-$C_3H_7$ | 0 | 0 | 3 | 0 | 1 | SO | 1 | 0 | H | H | (mp. 78–79° C.) |
| 69 | H | $n$-$C_3H_7$ | 0 | 0 | 3 | 0 | 1 | S | 1 | 0 | H | H | $n_D^{25}$ 1.5910 |
| 70 | H | $n$-$C_3H_7$ | 0 | 0 | 3 | 0 | 1 | S | 1 | 0 | 4-F | H | $n_D^{25}$ 1.5777 |
| 71 | $CH_3$ | $i$-$C_4H_9$ | 0 | 0 | 3 | 0 | 1 | S | 1 | 0 | H | H | $n_D^{25}$ 1.5789 |
| 72 | $CH_3$ | $n$-$C_3H_7$ | 0 | 0 | 1 | 1 | 1 | S | 1 | 0 | H | H | $n_D^{25}$ 1.5875 |
| 73 | $CH_3$ | $n$-$C_3H_7$ | 0 | 0 | 3 | 0 | 1 | S | 1 | 0 | 4-O-$C_6H_5$ | H | $n_D^{25}$ 1.6084 |
| 74 | $CH_3$ | $n$-$C_3H_7$ | 0 | 0 | 3 | 0 | 1 | S | 1 | 0 | 3-O-$C_6H_5$ | H | $n_D^{25}$ 1.6040 |
| 75 | Cl | $C_2H_5$ | 0 | 0 | 3 | 0 | 1 | S | 1 | 0 | H | H | $n_D^{25}$ 1.6035 |
| 76 | Cl | $n$-$C_5H_{11}$ | 0 | 0 | 3 | 0 | 1 | S | 1 | 0 | H | H | $n_D^{25}$ 1.5864 |
| 77 | $CH_3$ | $n$-$C_3H_7$ | 0 | 0 | 1 | 0 | 0 | — | 0 | 0 | H | H | $n_D^{25}$ 1.5835 |
| 78 | $CH_3$ | $n$-$C_3H_7$ | 0 | 1 | 2 | 0 | 1 | S | 1 | 0 | H | H | $n_D^{25}$ 1.5788 |
| 79 | $CH_3$ | $n$-$C_3H_7$ | 0 | 0 | 2 | 1 | 1 | S | 1 | 0 | H | H | $n_D^{25}$ 1.5802 |
| 80 | $CH_3$ | $n$-$C_4H_9$ | 0 | 0 | 3 | 0 | 1 | S | 1 | 0 | H | H | $n_D^{25}$ 1.5800 |
| 81 | H | $n$-$C_6H_{13}$ | 0 | 0 | 3 | 0 | 1 | S | 1 | 0 | H | H | $n_D^{25}$ 1.5730 |
| 82 | $CH_3$ | $n$-$C_3H_7$ | 0 | 0 | 3 | 0 | 1 | S | 1 | 0 | 2-Cl | 6-Cl | $n_D^{25}$ 1.6010 |

TABLE 1-continued $$\underset{R^2-S(O)_x}{\overset{R^1}{\bigcirc}}-O+CH_{\overline{a}}^{CH_3}(CH_2)_b(CH_{\overline{c}}^{CH_3})(Y)_y(CH_2)_d(CH_{\overline{e}}^{CH_3})\underset{R^4}{\overset{R^3}{\bigcirc}} \quad (I)$$

| Compound No. | $R^1$ | $R^2$ | x | a | b | c | y | Y | d | e | $R^3$ | $R^4$ | Physical property $n_D^{25}$(mp.), (bp.) |
|---|---|---|---|---|---|---|---|---|---|---|---|---|---|
| 83 | CH₃ | CH₃ | 0 | 0 | 3 | 0 | 1 | S | 1 | 0 | H | H | $n_D^{25}$ 1.6032 |
| 84 | CH₃ | C₂H₅ | 0 | 0 | 3 | 0 | 1 | S | 1 | 0 | H | H | $n_D^{25}$ 1.5943 |
| 85 | CH₃ | n-C₃H₇ | 0 | 0 | 3 | 0 | 1 | S | 0 | 1 | H | H | $n_D^{25}$ 1.5802 |
| 86 | CH₃ | n-C₃H₇ | 0 | 0 | 3 | 0 | 1 | O | 0 | 0 | 3-CF₃ | H | $n_D^{25}$ 1.5343 |
| 87 | CH₃ | n-C₃H₇ | 0 | 0 | 3 | 0 | 1 | O | 0 | 0 | 4-SCH₃ | 3-CH₃ | $n_D^{25}$ 1.5894 |
| 88 | CH₃ | n-C₃H₇ | 0 | 0 | 3 | 0 | 1 | S | 1 | 0 | 4-t-C₄H₉ | H | $n_D^{25}$ 1.5706 |
| 89 | CH₃ | n-C₃H₇ | 0 | 0 | 5 | 0 | 1 | S | 0 | 0 | 4-Br | H | (mp. 42–43° C.) |
| 90 | CH₃ | n-C₃H₇ | 0 | 0 | 3 | 0 | 1 | O | 0 | 0 | H | H | $n_D^{25}$ 1.5726 |
| 91 | CH₃ | n-C₃H₇ | 0 | 0 | 3 | 0 | 1 | O | 0 | 0 | 4-OCH₃ | H | $n_D^{25}$ 1.5653 |
| 92 | CH₃ | n-C₃H₇ | 0 | 0 | 3 | 0 | 1 | O | 0 | 0 | 4-Br | H | $n_D^{25}$ 1.5849 |
| 93 | CH₃ | n-C₃H₇ | 0 | 0 | 3 | 0 | 1 | O | 0 | 0 | 4-SCH₃ | H | (mp. 45–46° C.) |
| 94 | CH₃ | n-C₃H₇ | 0 | 0 | 3 | 0 | 1 | O | 0 | 0 | 3-SC₃H₇(n) | 4-CH₃ | (mp. 61.5–62.5° C.) |
| 95 | CH₃ | n-C₃H₇ | 0 | 0 | 3 | 0 | 1 | O | 0 | 0 | 4-O-C₆H₅ | H | $n_D^{25}$ 1.5915 |
| 96 | CH₃ | n-C₃H₇ | 1 | 0 | 3 | 0 | 1 | O | 0 | 0 | 4-O-C₆H₅ | H | $n_D^{25}$ 1.5847 |
| 97 | CH₃ | n-C₃H₇ | 2 | 0 | 3 | 0 | 1 | O | 0 | 0 | 4-O-C₆H₅ | H | $n_D^{25}$ 1.5755 |

FORMULATION EXAMPLE

Formulation Example 1: Emulsifiable Concentration 20 parts of a compound of the present invention were dissolved in 65 parts of a xylene/methylnaphthalene mixture. 15 parts of a mixture of an alkylphenol/ethylene oxide condensate and calcium alkylbenzenesulfonate in a ratio of 8:2 were mixed with the obtained solution to prepare an emulsifiable concentration. This emulsifiable concentration may be used as a spreading agent by diluting with water.

Formulation Example 2: Wettable Powder 20 parts of a compound of the present invention were mixed with 35 parts of kaolin, 30 parts of clay and 7.5 parts of diatomaceous earth. 7.5 parts of a mixture of sodium laurate and sodium dinaphthylmethanesulfonate in a ratio of 1:1 were added to the obtained mixture. The resulting mixture was finely ground to prepare a powder. This powder may be used as a spreading agent by diluting with water.

Formulation Example 3: Dust 1 part of a compound of the present invention was mixed with 97 parts of a mixture of talc and calcium carbonate in a ratio of 1:1. The resulting mixture was ground to prepare a homogeneously dispersed mixture. 2 parts of silicic anhydride were added to this mixture. The resulting mixture was mixed and ground to prepare a dust. This dust may be used as a spreading agent as such.

Formulation Example 4: Granule 2 parts of a compound of the present invention were mixed with 48 parts of finely powdered bentonite, 48 parts of talc and 2 parts of sodium ligninsulfonate, followed by the addition of water. The resulting mixture was kneaded until it became homogeneous. The mixture was granulated by passing it through an injection molding machine and adjusted to a granular size of 0.6 to 1 mm by passing the granule thus molded through a spherizer and a drying screen classifier. The obtained granule may be directly spreaded on the surface of paddy fields and uplands as such.

Formulation Example 5: Oil

A mixture of 0.1 part of a compound of the present invention and 0.5 part of piperonyl butoxide was dissolved in such as amount of illuminating kerosine as to give the total volume of 100 parts to prepare an oil. This oil may be used as such.

Formulation Example 6: Aerosol 0.4 part of a compound of the present invention, 20 parts of piperonyl butoxide, 6 parts of xylene and 7.6 parts of deodorized kerosine were mixed and dissolved. After filling the mixture into an aerosol container, a valve was fitted. 86 parts of Freon were introduced into the container through the valve under pressure to obtain an aerosol.

The effects of the present invention will be described by the following Test Examples.

The compound used in the Test Examples as a control are the following reference compounds (A), (B) and (C). These compounds were also tested according to the same method as the one for the test of the compounds of the present invention.

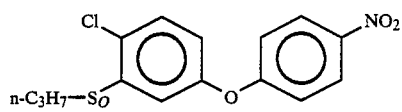
(A)

(Japanese Patent Publication No. 9732/1977)

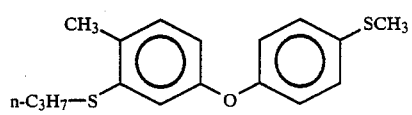
(B)

(Japanese Patent Publication No. 31932/1977)

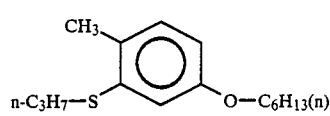
(C)

(Japanese Patent Publication No. 35162/1982)

TEST EXAMPLE

Test Example 1: Effect on adults of *Tetranychus urticae*

The compounds of the present invention and the reference compounds were formulated according to the same procedures as the ones described in Formulation Examples 1 and 2, into 20% wettable powders when they were crystals, or into 20% emulsifiable concentration when they were oils, and were used for this test.

Testing method: The primary leaf of a kidney bean grown in a pot (9 cm across) was trimmed to a size of about 3 cm×3 cm. 15 female adult mites susceptible to organophosphorus insecticides (collected in Sapporo) were transferred carefully onto the leaf using a small brush. The plant was left in a greenhouse controlled at 25° C. for one day. After one day, dead and abnormal mites were taken out of the leaf. The mites on the leaf were dipped in a solution, adjusted to 400 ppm of effective components of every tested compounds by dilution with water, for 10 seconds. After that, the plant was kept still in the greenhouse again. 48 hours after the treatment, the number of live and dead mites was counted under a stereomicroscope to calculative the mortality. The results are shown in Table 2.

TABLE 2

| Test compound | | Mortality (%) |
|---|---|---|
| The present compound no. | 1 | 67 |
| | 2 | 80 |
| | 3 | 80 |
| | 6 | 67 |
| | 7 | 80 |
| | 12 | 67 |
| | 15 | •60 |
| | 18 | 100 |
| | 19 | 100 |
| | 21 | 100 |
| | 22 | 100 |
| | 23 | 60 |
| | 24 | 100 |
| | 25 | 100 |
| | 26 | 100 |
| | 27 | 100 |
| | 28 | 100 |
| | 29 | 60 |

TABLE 2-continued

| Test compound | | Mortality (%) |
|---|---|---|
| | 30 | 100 |
| | 31 | 100 |
| | 32 | 100 |
| | 33 | 100 |
| | 34 | 100 |
| | 35 | 100 |
| | 36 | 100 |
| | 37 | 100 |
| | 38 | 100 |
| | 39 | 100 |
| | 40 | 100 |
| | 41 | 100 |
| | 42 | 100 |
| | 43 | 100 |
| | 44 | 100 |
| | 45 | 100 |
| | 46 | 100 |
| | 47 | 100 |
| | 48 | 100 |
| | 49 | 100 |
| | 50 | 100 |
| | 51 | 100 |
| | 52 | 100 |
| | 53 | 100 |
| | 54 | 100 |
| | 55 | 100 |
| | 56 | 100 |
| | 57 | 100 |
| | 58 | 100 |
| | 59 | 100 |
| | 60 | 100 |
| | 61 | 100 |
| | 62 | 100 |
| | 63 | 80 |
| | 64 | 80 |
| | 65 | 100 |
| | 66 | 100 |
| | 67 | 100 |
| | 68 | 100 |
| | 69 | 93 |
| | 70 | 100 |
| | 71 | 100 |
| | 72 | 100 |
| | 73 | 100 |
| | 74 | 100 |
| | 75 | 80 |
| | 76 | 93 |
| | 77 | 93 |
| | 78 | 80 |
| | 79 | 100 |
| | 80 | 93 |
| | 81 | 93 |
| | 82 | 80 |
| | 83 | 80 |
| | 84 | 100 |
| | 85 | 100 |
| | 86 | 100 |
| | 87 | 100 |
| | 88 | 100 |
| | 89 | 100 |
| | 90 | 100 |
| | 91 | 100 |
| | 92 | 100 |
| | 93 | 100 |
| | 95 | 100 |
| | 96 | 100 |
| Reference compound | A | 100 |
| | B | 100 |
| | C | 100 |
| Not treated | | 0 |

Test Example 2: Effect on adults, eggs and nymphs of *Tetranychus uritcae* of strains resistant to organophosphorus insecticides and dicofol (Kelthane ®)

The compounds of the present invention and the reference compounds were formulated according to the same procedures as the ones described in Formulation Examples 1 and 2, into 20% wettable powder when they were crystals, or into 20% emulsifiable concentration when they were oils, and were used for this test.

Testing method: A sheet of urethane imbibed with water, 1.5 cm thick, was put in a laboratory dish, and a sheet of filter paper was placed on the urethane sheet. A primary leaf of a kidney bean was trimmed to a size of 2 cm×2 cm, and 2 sheets of the leaf, whereof the under surface was turned over, were put a little apart from each other on the paper. In case of adults test, 40 female adults of strain resistant organophosphorus insecticides and dicofol (Keltane®) (collected in Nagano) were transferred by a small brush, and abnormal mites were removed after 24 hours. In case of eggs and nymphs tests, 5 female adults a dish of the same strain were transferred by a small brush, and, after laying eggs for 24 hours, female mites were removed. The number of eggs was recorded. Then, 5 ml of solutions, diluted by water to 200 ppm of effective components of every tested compounds, were spread on the dishes by means of MIZUHO rotary spreading tower under a pressure of 260 to 280 mmHg. After the treatment by the compounds, the dishes were kept still in a temperature-controlled chamber (25°±2° C.). Discrimination of live and dead mites was performed 2 days after the treatment about adults, or 7 days about eggs, by counting the number of unhatched eggs, and the numbers of dead and live nymphs were recorded to calculate the mortality. In addition, phytotoxicity to the host plant, kidney bean, was determined. Those results are shown in Table 3.

TABLE 3

| Tested compound | | Mortality (%) Adults | Eggs | Nymphs | Phytotoxicity* |
|---|---|---|---|---|---|
| The present compound no. | 27 | 80 | 100 | — | ± |
| | 28 | 60 | 100 | — | — |
| | 33 | 95 | 100 | — | — |
| | 36 | 100 | 100 | — | — |
| | 37 | 70 | 68 | 80 | — |
| | 38 | 100 | 100 | — | — |
| | 40 | 63 | 95 | 100 | — |
| | 41 | 80 | 90 | 100 | — |
| | 42 | 100 | 100 | — | — |
| | 43 | 100 | 100 | — | — |
| | 44 | 60 | 80 | 100 | — |
| | 45 | 85 | 80 | 70 | — |
| | 46 | 90 | 70 | 75 | — |
| | 47 | 100 | 100 | — | — |
| | 48 | 100 | 100 | — | — |
| | 49 | 100 | 100 | — | — |
| | 50 | 100 | 100 | — | — |
| | 51 | 80 | 95 | 100 | — |
| | 52 | 90 | 90 | 100 | — |
| | 53 | 100 | 75 | 80 | — |
| | 55 | 100 | 70 | 100 | — |
| | 56 | 100 | 70 | 100 | — |
| | 61 | 100 | 60 | 100 | — |
| | 65 | 70 | 100 | — | — |
| | 66 | 70 | 85 | 100 | — |
| | 67 | 80 | 80 | 100 | — |
| | 68 | 100 | 80 | 100 | — |
| | 70 | 100 | 100 | — | — |
| | 71 | 100 | 90 | 100 | — |
| | 72 | 90 | 90 | 90 | — |
| | 73 | 100 | 85 | 100 | — |
| | 74 | 90 | 80 | 75 | — |
| | 75 | 85 | 100 | — | — |
| | 76 | 70 | 100 | — | — |
| | 77 | 95 | 100 | — | — |
| | 78 | 100 | 100 | — | — |
| | 79 | 100 | 100 | — | — |
| | 80 | 70 | 100 | — | ± |
| | 81 | 70 | 80 | 75 | — |

TABLE 3-continued

| Tested compound | | Mortality (%) Adults | Eggs | Nymphs | Phytotoxicity* |
|---|---|---|---|---|---|
| | 82 | 80 | 100 | — | — |
| | 83 | 95 | 100 | — | — |
| | 84 | 100 | 100 | — | — |
| | 85 | 100 | 100 | — | — |
| | 86 | 100 | 100 | — | — |
| | 87 | 100 | 100 | — | — |
| | 88 | 100 | 100 | — | — |
| | 89 | 100 | 100 | — | — |
| Reference compound | A | 29 | 100 | — | ++ |
| | B | 81 | 100 | — | ++ |
| | C | 64 | 100 | — | ± |
| Dicofol (Kelthane ®) | | 5 | 33 | 20 | — |

*Phytotoxicity
+++ severe ++ moderate + little ± slight − more

Test Example 3: Effect on adults, eggs and nymphs of *Panonychus citri*

The same procedure as described in Test Example 2 were repeated, except that *Panonychus citri* (collected in Okitsu) was used in place of *Tetranychus urtieae*, and a leaf of Unshu Mandarin in place of kidney bean. The results are shown in Table 4.

TABLE 4

| Tested compound | | Mortality (%) Adults | Eggs | Nymphs | Phytotoxicity* |
|---|---|---|---|---|---|
| The present compound no. | 36 | 100 | 65 | 100 | — |
| | 41 | 100 | 100 | — | — |
| | 42 | 100 | 80 | 100 | — |
| | 43 | 88 | 94 | 100 | — |
| | 44 | 100 | 75 | 100 | — |

*see Table 3

Test Example 4: Effect on *Nilaparvata lugens*

The compounds of the present invention and the reference compounds were formulated according to the same procedure as the ones described in Formulation Examples 1 and 2 into 20% wettable powders or into 20% emulsifiable concentration and tested, similarly to Test Example 1.

Testing method: 5 to 6 rice plants in the tri- to tetra-foliate stages were dipped in solutions diluted with water to 200 ppm of effective components of every tested compounds, for 15 seconds. After air-dried, the plants were placed in a glass cylinder (4.5 cm across, 15 cm high). Then, 10 female adults of *Nilaparvata lugens* (collected in Kaseda) were transferred into the cylinder. After covered with a wire mesh, the cylinder was kept still in a glass greenhouse. 8 days after treatment, the numbers of live and dead insects were counted to calculate the mortality. The results shown in Table 5 are average of two replications.

TABLE 5

| Test compound | | Mortality (%) |
|---|---|---|
| The present compound no. | 41 | 80 |
| | 45 | 90 |
| | 48 | 80 |
| | 52 | 100 |
| | 53 | 70 |
| | 55 | 70 |
| | 56 | 100 |
| | 57 | 70 |
| | 62 | 100 |
| | 67 | 80 |
| | 69 | 90 |
| | 71 | 100 |

TABLE 5-continued

| Test compound | | Mortality (%) |
|---|---|---|
| | 72 | 100 |
| | 77 | 100 |
| | 86 | 100 |
| Reference compound | A | 0 |
| | B | 10 |
| | C | 0 |
| Not treated | | 10 |

Test Example 5: Effect on Larvae of *Plutella xylostella*

The compounds of the present invention and the reference compounds were formulated according to the same procedures as the ones described in Formulation Examples 1 and 2, into 20% wettable powders when they were crystals, or into 20% emulsifiable concentration when they were oils, and were used for this test.

Testing method: A cabbage leaf of a medium size cut from cabbage grown to decafoliate state was dipped in a solution diluted with water to 200 ppm of effective components of every tested compounds, for 15 seconds. After air-dried, the leaf was placed in a plastic container (9 cm across). 15 larvae (third instar) of *Plutella xylostella* were transferred into the container. With covering by a lid having several pin holes, the container was left in a temperature-controlled chamber at 25° C. 10 days after the treatment, the numbers of live and dead insects were counted to calculate the mortality. The results shown in Table 6 are averages of two replications.

TABLE 6

| Test compound | | Mortality (%) |
|---|---|---|
| The present compound no. | 36 | 100 |
| | 47 | 100 |
| | 48 | 100 |
| | 49 | 100 |
| | 51 | 100 |
| | 52 | 100 |
| | 55 | 100 |
| | 67 | 100 |
| | 68 | 100 |
| | 69 | 100 |
| | 70 | 100 |
| | 80 | 100 |
| | 84 | 100 |
| | 85 | 100 |
| Reference compound | A | 20 |
| | B | 10 |
| | C | 10 |
| Not treated | | 0 |

What we claim is:

1. An acaricidal or insecticidal composition which comprises, as an effective component, an effective amount of a compound of the formula:

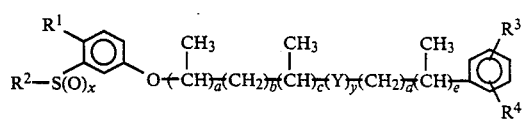

wherein
R$^1$ is chloro or methyl,
R$^2$ is ethyl, n-propyl, n-butyl, isobutyl, n-amyl or n-hexyl,
R$^3$ is hydrogen, chloro, fluoro, —CF$_3$, nitro, methyl, ethyl, t-butyl, methoxy, methlthio, ethylthio or n-propylthio,
R$^4$ is hydrogen, chloro or methyl,
Y is oxygen, sulfur, sulfinyl or sulfonyl,
x is 0 or 1,
y is 1,
a is 0 or 1,
b is an integer of 1 to 6,
c is 0 or 1,
d is 0, 1 or 2,
e is 0 or 1,
and the sum of a, b, c, d, and e is seven or below.

2. A method for killing acarid(s) or insect(s), which comprises applying an effective amount of the compound of the formula:

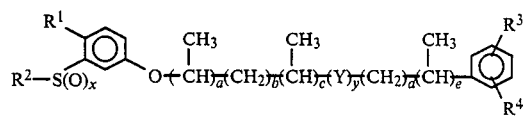

wherein
R$^1$ is chloro or methyl,
R$^2$ is ethyl, n-propyl, n-butyl, isobutyl, n-amyl or n-hexyl,
R$^3$ is hydrogen, chloro, fluoro, —CF$_3$, nitro, methyl, ethyl, t-butyl, methoxy, methylthio, ethylthio or n-propylthio,
R$^4$ is hydrogen, chloro or methyl,
Y is oxygen, sulfur, sulfinyl or sulfonyl,
x is 0 or 1,
y is 1,
a is 0 or 1,
b is an integer of 1 to 6,
c is 0 or 1,
d is 0, 1 or 2,
e is 0 or 1,
and the sum of a, b, c, d and e is seven or below.

3. A compound selected from the group consisting of:
1-(4-methyl-3-n-propylthiophenoxy)-2-phenoxy-ethane,
1-(4-methyl-3-n-propylsulfinylphenoxy)-2-phenoxy-ethane,
1,2-bis(4-methyl-3-n-propylthiophenoxy)-ethane,
1-(4-methyl-3-n-propylthiophenoxy)-2-(4-chlorophenylthio)ethane,
1-(4-methyl-3-n-propylthiophenoxy)-3-benzylthio-n-propane,
1-(4-methyl-3-n-propylthiophenoxy)-3-(4-chlorophenylthio)-n-propane,
1-(4-methyl-3-n-propylthiophenoxy)-5-(4-chlorophenylthio)-n-pentane,
1-(4-methyl-3-n-propylthiophenoxy)-6-(4-chlorophenylthio)-n-hexane,
di-(4-methyl-3-n-propylthiophenoxy)-ethylether,
1-(4-methyl-3-n-propylthiophenoxy)-4-(4-chlorobenzylthio)-n-butane,
1-(4-methyl-3-n-propylthiophenoxy)-4-benzylthio-n-butane,
1-(4-methyl-3-n-propylthiophenoxy)-3-(4-chlorobenzylthio)-n-propane,
1-(4-methyl-3-n-propylthiophenoxy)-3-(4-methylbenzylthio)-n-propane,
1-(4-methyl-3-n-propylthiophenoxy)-5-benzylthio-n-pentane,
1-(4-methyl-3-n-propylthiophenoxy)-6-benzylthio-n-hexane,
1-(4-methyl-3-n-propylthiophenoxy)-3-benzylthio-n-propane,
1-(4-methyl-3-n-propylthiophenoxy)-3-benzylsulfinyl-n-propane, 1-(4-methyl-3-n-propylthiophenoxy)-3-benzylsulfonyl-n-propane,
1-(4-methyl-3-n-propylsulfinylphenoxy)-3-benzylsulfinyl-n-propane,
1-(4-methyl-3-n-propylsulfinylphenoxy)-3-benzylsulfonyl-n-propane,
1-(4-chloro-3-n-propylthiophenoxy)-3-benzyl-n-propane,
1-(4-methyl-3-n-propylthiophenoxy)-2-benzyl-ethane,
1-(4-methyl-3-n-propylsulfinylphenoxy)-2-benzyl-ethane,
1-(4-methyl-3-n-propylthiophenoxy)-3-(4-methylbenzylthio)-n-propane,
1-(4-methyl-3-n-propylthiophenoxy)-3-benzyloxy-n-propane,
1-(4-methyl-3-n-propylsulfinylphenyl)-3-benzyloxy-n-propane,
(4-methyl-3-n-propylthiophenoxy)-benzylthio-methane,
1-(4-methyl-3-n-propylthiophenoxy)-4-(4-methylbenzylthio)-n-butane,
1-(4-methyl-3-n-propylthiophenoxy)-2-(2-phenylethylthio)-ethane,
1-(4-methyl-3-n-propylthiophenoxy)-3-phenylthio-n-propane,
1-(4-methyl-3-n-propylthiophenoxy)-4-phenylthio-n-butane,
1-(4-chloro-3-n-propylsulfinylphenoxy)-2-benzylthio-n-propane,
1-(4-chloro-3-n-propylthiophenoxy)-3-benzylsulfinyl-n-propane,
1-(4-methyl-3-n-isobutylthiophenoxy)-3-benzylthio-n-propane,
1-(4-methyl-3-n-propylthiophenoxy)-2-benzylthio-n-propane,
1-(4-chloro-3-n-ethylthiophenoxy)-3-benzylthio-n-propane,
1-(4-chloro-3-n-pentylthiophenoxy)-3-benzylthio-n-propane,
4-methyl-3-n-propylthio-1-benzyloxybenzene,
1-benzylthio-3-(4-methyl-3-n-propylthiophenoxy)-n-butane,
3-(benzylthio-1-(4-methyl-3-n-propylthiophenoxy)-n-butane,
1-(4-methyl-3-n-butylthiophenoxy)-3-benzylthio-n-propane,
1-(4-methyl-3-n-propylthiophenoxy)-3-(2,6-dichlorobenzylthio)-n-propane,
1-(4-methyl-3-ethylthiophenoxy)-3-benzylthio-n-propane,
1-(4-methyl-3-n-propylthiophenoxy)-3-(α-methylbenzylthio)-n-propane,
1-(4-methyl-3-n-propylthiophenoxy)-3-(3-trifluoromethylphenoxy)-n-propane,
1-(4-methyl-3-n-propylthiophenoxy)-3-(3-methyl-4-methylthiophenoxy)-n-propane,
1-(4-methyl-3-n-propylthiophenoxy)-3-(4-tert-butylbenzylthio)-n-propane, and
1-(4-methyl-3-n-propylthiophenoxy)-5-(4-bromophenylthio)-n-pentane.

* * * * *

UNITED STATES PATENT AND TRADEMARK OFFICE
CERTIFICATE OF CORRECTION

PATENT NO. : 4,931,474
DATED : June 5, 1990
INVENTOR(S) : Shoichi Kato, et al.

It is certified that error appears in the above-identified patent and that said Letters Patent is hereby corrected as shown below:

Column 25, line 66, change "methlthio" to --methylthio--.

Column 26, line 11, after "applying" insert --to said acarid(s) or insect(s) or locus thereof--.

Column 27, line 16, change "propylsulfinlphenyl" to --propylsulfinylphenoxy--.

Column 28, line 12, change "3-(benzylthio" to --3-benzylthio--.

Signed and Sealed this

Fourth Day of February, 1992

Attest:

HARRY F. MANBECK, JR.

*Attesting Officer*　　　　　*Commissioner of Patents and Trademarks*